United States Patent

Wolf

[11] Patent Number: 5,842,326
[45] Date of Patent: Dec. 1, 1998

[54] METHOD FOR FABRICATING A STERILE READY-PACK AND A CONTAINER FOR SUCH A READY-PACK

[75] Inventor: Erich Wolf, Overath, Germany

[73] Assignee: Farco-Pharma Gesellschaft Mit Beschränkter Haftung Pharmazeutische Präparate, Köln, Germany

[21] Appl. No.: 571,896
[22] PCT Filed: Jun. 16, 1994
[86] PCT No.: PCT/DE94/00680
 § 371 Date: Dec. 18, 1995
 § 102(e) Date: Dec. 18, 1995
[87] PCT Pub. No.: WO95/00180
 PCT Pub. Date: Jan. 5, 1995

[30] Foreign Application Priority Data

Jun. 17, 1993 [DE] Germany ............... 43 20 066.4

[51] Int. Cl.⁶ ........................... B65B 55/02
[52] U.S. Cl. .................. 53/425; 422/25; 422/26
[58] Field of Search .............. 53/425; 206/439; 422/25, 26

[56] References Cited

U.S. PATENT DOCUMENTS

| | | |
|---|---|---|
| 2,004,079 | 6/1935 | McManus . |
| 3,460,742 | 8/1969 | Langdon ............................. 206/439 |
| 3,468,471 | 9/1969 | Linder ................................. 206/439 X |
| 3,507,386 | 4/1970 | Ishii et al. ........................... 206/439 X |
| 3,945,796 | 3/1976 | Nagamatsu et al. ................ 422/26 X |
| 4,225,555 | 9/1980 | Fahlvik et al. ..................... 422/25 |
| 4,263,258 | 4/1981 | Kalasek .............................. 422/26 X |
| 4,467,588 | 8/1984 | Carveth . |
| 4,603,538 | 8/1986 | Shave ................................. 53/425 |
| 4,718,463 | 1/1988 | Jurgens et al. . |
| 4,828,797 | 5/1989 | Zwarun et al. . |
| 4,941,883 | 7/1990 | Venturini . |
| 4,998,400 | 3/1991 | Suzuki et al. ...................... 53/425 |
| 5,033,252 | 7/1991 | Carter ................................ 53/425 |
| 5,207,983 | 5/1993 | Liebert et al. . |
| 5,373,684 | 12/1994 | Vacca ................................. 53/425 |
| 5,390,792 | 2/1995 | Van Ness et al. .................. 206/439 |
| 5,418,022 | 5/1995 | Anderson et al. .................. 206/439 X |
| 5,439,643 | 8/1995 | Liebert .............................. 422/25 |
| 5,459,978 | 10/1995 | Weiss et al. ....................... 53/425 |

FOREIGN PATENT DOCUMENTS

| | | |
|---|---|---|
| 0227401 | 7/1987 | European Pat. Off. . |
| 0322134 | 6/1989 | European Pat. Off. . |
| 2521906 | 8/1983 | France . |
| 27 11 732.4 | 9/1977 | Germany . |
| 87 06 916.4 | 9/1987 | Germany . |
| 39 16 101.3 | 11/1990 | Germany . |

Primary Examiner—Daniel Moon
Attorney, Agent, or Firm—Darby & Darby

[57] ABSTRACT

A method for a single step sterilization of a ready-pack, such as a blister pack, in an autoclave is described. The ready pack includes a container, such as a syringe, filled with a substance. The environment in the autoclave, that is, the temperature, the heating period and, preferably, the pressure is controlled to sterilize simultaneously the ready-pack and its contents by circulating steam in the autoclave. The steam penetrates into the blister pack through a steam-permeable base. The temperature is maintained between about 120° C. to 130° C. for about 15–20 minutes.

8 Claims, 2 Drawing Sheets

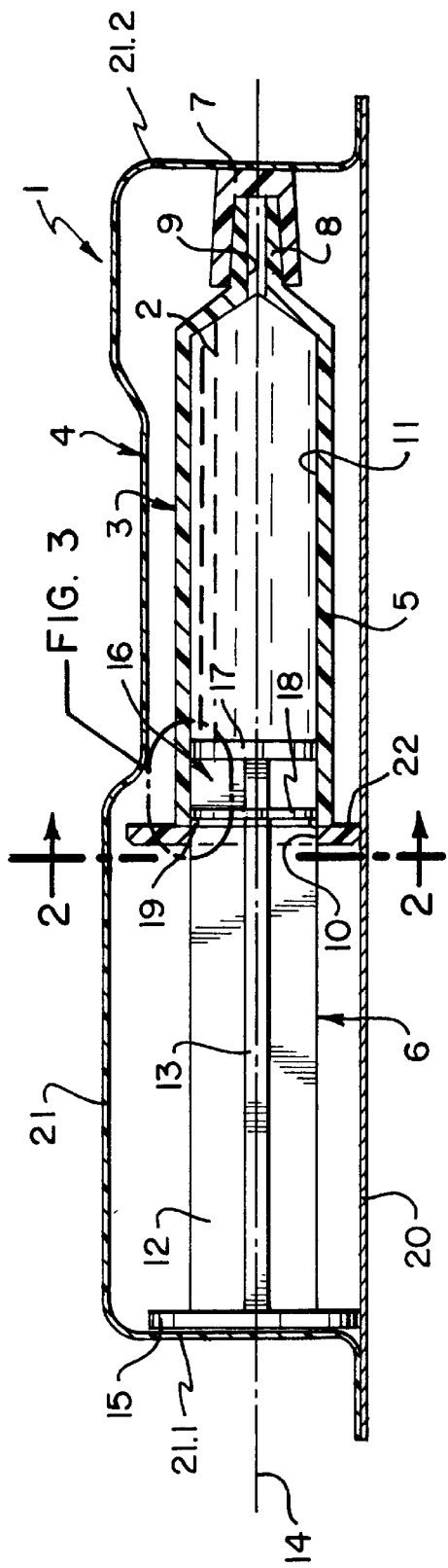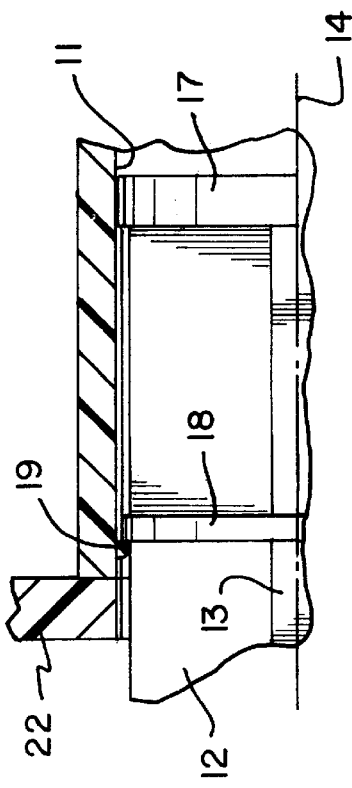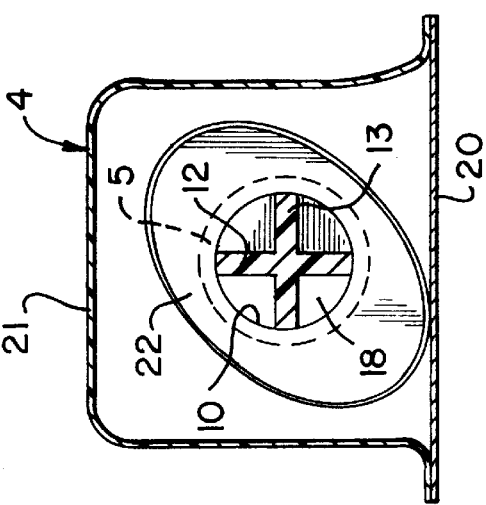

METHOD FOR FABRICATING A STERILE READY-PACK AND A CONTAINER FOR SUCH A READY-PACK

TECHNICAL FIELD

The invention relates to a method for fabricating a sterile ready-pack and a container for such a ready-pack with at least one sealed-in, especially blister-type container with a filling, especially with a medication, a diagnostic means, or the like, especially a syringe, bag, bottle, or other medical utility object, whose package, especially a blister pack, has a region which is permeable preferably to the diffusion of steam, and for the rest is tight, such that the material used for the container is stable at least 125° C. (degrees Celsius), preferably at 130° C., and such that the sealed, tightly closed pack is exposed to an autoclaving process.

When water is heated in a closed pressure vessel, an over-pressure of 1 bar is reached at 121° C. 15 to 20 minutes action of the "confined" steam is sufficient to kill all microorganisms capable of reproduction.

PRIOR ART

With a known ready-pack of this kind, the individual parts of the plastic syringe are gassed with ethylene oxide in order to sterilize them. Then the syringe is assembled under sterile conditions and is filled with the previously sterilized fill under aseptic conditions, and is then sealed. Then the filled syringe is blistered into a sealed package, which then is gassed with ethylene oxide for sterilization. The gas then penetrates through porosities in the covering and flushes the syringe from the outside.

With this method, it is expensive to fabricate the filled syringe, since this is done under sterile conditions. Also, expensive precautions must be taken to prevent ethylene oxide residues or decomposition products from finding their way from the gassing process of the syringe and of the finished pack into the fill of the syringe and remaining there.

The U.S. Pat. No. 4,828,797 shows the fabrication of a biological test kid [sic, but evidently should be "kit"] by means of which the effectiveness e.g. of an ethylene oxide sterilization process can be tested. Here, an open plastic throw-away syringe in a blister is freed of germs by means of a Tyvek (registered trademark) film through sterilization. A test strip is here situated in the interior of the syringe, and it changes color if the sterilization is adequate, e.g. through ethylene oxide.

The U.S. Pat. No. 5,033,252 discloses a sterilization method, in which a bottle filled with a sterile salt solution is placed into a blister, which subsequently is exposed to gassing by ethylene oxide or by confined steam. The exterior of the bottle is thus freed of germs. This method presupposes that the bottle must be filled completely, without any residual air in its interior, and that the bottle must be filled under aseptic conditions. This regularly involves an overflow of the fill, in order to assure that no air is present in the interior of the bottle. Consequently, the bottle itself and its environment must be cleaned after the filling process. In conjunction with the aseptic filling process and sealing process, this method is very expensive and consequently not very economical.

The EP 0 227 401 B1 describes a method for the end sterilization of a plastic syringe together with its content (liquid) by means of steam and a support pressure. This method has already been described for ready-to-use syringes made of glass, in detail and with pictures, in Venten & Hoppert, Pharm. Ind., Volume 40 (1978), Page 665 ff Point 4.

EXPLANATION OF THE INVENTION

The first object of the invention is to simplify the fabrication of a sterile ready-pack of the type mentioned in the introduction, and to make possible economic and ecologically friendly fabrication with autoclaving of the final package.

The inventive method is specified by the features of claim 1. Advantageous designs and modifications are the subject of the subclaims.

The inventive method accordingly is characterized in that, in a single operating step, both the fill is sterilized for at least 15 minutes, preferably 20 minutes, at a minimum of 121° C., by means of a steam-air mixture rotary method, and the outer surface of the container as well as the package are also sterilized.

According to the invention, it has been recognized that it is especially economical to autoclave the ready-pack in one step, so that both the inside of the pack (blister), the outside of the closed container, and also the fill material (liquid, gel-like, or paste-like medication) are sterilized in a single treatment process.

An especially preferred modification of the inventive method is characterized in that several ready-packs are disposed in one packing unit (folding box), which has a region that is permeable to steam, and that the internal temperature of the liquid, gel-like, or paste-like medication is measured in at least one ready-pack, preferably in at least two ready-packs, of the entire autoclave charge.

In an especially advantageous manner, the procedure furthermore can be such that, during the entire sterilization cycle, the pressure and the moisture content are measured, and the sterilization cycle is regulated in dependence on the measured data, such that the pressure preferably can be changed at a specifiable rate.

Since the temperature is measured in the medication (or material) itself, the perfect progress of the sterilization cycle can be assured and documented directly and without any doubt. If the measured temperature is too low, a control mechanism activates a heating device which directly or indirectly brings addition heat (steam) into the autoclave chamber. Since the pressure and the moisture can be controlled at the same time, it is possible to prevent damage of the ready-pack or of the packing unit due to pressure differences or due to condensing water. The pressure can be changed preferably at a rate of ±0.1 bar per 5 minutes. For example, a pressure of 3.0 bar is provided as the maximum support pressure during cooling. In order to make the reduction of pressure possible, the autoclave has an evacuation mechanism which is controlled in accordance with the measured data.

Cardboard, in a preferred folding-box design, is used as the material for the packing unit, which contains several ready-packs. This carton preferably is perforated at least in part, so that the steam can reach the interior of the packing unit without great resistance. For example, a paper bag can also be used for the packing unit. From the point of view of economy and of the disposal of the ready-pack, it is advantageous to make the area that is permeable to steam out of paper. Consequently, no disposal problems arise in connection with the cardboard structure of the packing unit, since the above materials can readily be recycled.

In a preferred embodiment, the sterilization by steam takes place on filled, blistered syringes packed by tens in folding boxes. The moisture of the air-steam mixture is regulated to an optimal, empirically determined level at the steam/condensate boundary. This assures rapid heat transfer through the preferably perforated folding box and through the paper of the ready-pack to the outside of the syringe. The outside of the syringe must be heated and wetted in such a way that a temperature of 121° C. is reached, preferably for 20 minutes, in its fill (liquid, gel-like, or paste-like medication).

The inventive optimization of the steam/condensate range during the autoclaving process prevents visual changes (water spots) both on the sterile paper of the blister and on the folding box.

In contrast to the syringe used in the known method, the syringe used in accordance with the invention is stable at 125° C. and consequently can be sterilized with confined steam. As a result, it becomes possible to sterilize the ready-to-go sealed ready-pack thermally. When the ready-pack is gassed with ethylene oxide, the sterilization acts only on the exterior of the syringe body; in contrast, sterilization by a steam-air mixture can also sterilize the interior of the syringe body (container) and its fill. As a result, expensive production measures for producing a syringe with a sterile fill can be avoided. Furthermore, since no microbicidal gasses need to be used for the sterilization, the problem of the residues of such gasses no longer exists.

Furthermore, an aseptic fill process of a liquid, gel-like, or paste-like medication is no longer necessary. As is well known, such a process involves the risk of microbial contamination, in contrast to a final sterilization of the medication in the closed final container.

It is well known that sterilization by autoclaving at 121° C. for 20 minutes results in adequate sterilization. However, one must assure, by a proper choice of the sterilization time and temperature, that the sterilization conditions, namely 121° C. and 20 minutes' duration, also prevail in the innermost part of the fill. In view of the unavoidable temperature gradient, a core temperature of 121° C. in the fill requires a temperature of several degrees Celsius above this for the syringe body. This is the reason why the syringe body must have a temperature stability that is at least several degrees Celsius higher, even though 121° C. is sufficient for sterilization.

A thermally stable plastic, especially polypropylene or glass, is especially suited as a material for the syringe. According to the invention, a piston rod can be inserted into the syringe, parts of which have a rubber sealing device.

The inventive method for fabricating a ready-pack with a syringe preferably is performed in such a way that an empty syringe, equipped with a discharge cone, is held ready with its piston advanced to the discharge position, that a dose of the fill is pressed into the ready syringe through the discharge cone and thus the piston is pressed back, that the discharge cone of the filled syringe is sealed with a sealing cap which consists of a flexible material that is stable at least at 121° C., preferably of a temperature-stable rubber or plastic, that the filled, sealed syringe is placed into a blister-type package, that the blister is closed and sealed, that the ready-pack or a packing unit with several ready-packs is heated by steam all the way through to 121° C. in the autoclave, preferably after previous evacuation, and is maintained heated all the way through at 121° C. for at least 20 minutes, and that the ready-pack is then cooled slowly, preferably with the introduction of a support pressure, and thus is decompressed, and that its moisture is completely removed by single or multiple evacuation.

Another variant of the inventive method is characterized in that a syringe without a piston rod is kept ready, whose discharge cylinder is closed by means of a closure cap or by an injection needle rigidly connected to the syringe and closed with a needle protection cap, or by an applicator, which consists of an elastic material that is stable at least at 121° C., the fill is dosed into the ready syringe from the opening for the piston rod, the piston rod is sealingly introduced into the filled syringe, the filled, closed syringe is inserted into a blister, the blister closure is now sealed, the ready-pack or a packing unit containing one or more ready-packs is heated to 121° C. by steam in the autoclave, preferably after previous evacuation, and is kept heated at 121° C. for at least 20 minutes, and the ready-pack is then slowly cooled, preferably while a support pressure is introduced, and thus is decompressed.

In a preferred design, the container is placed into the ready-pack or the wall of the ready-pack is fitted to the container so that a linear expansion or linear displacement, which may sometimes occur due to the sterilization (heating) process, is at least partially suppressed by the wall of the container. Thus, especially in the case of syringes, the piston can be prevented from escaping as a result of the heating of the filling and of the residual air bubble. In this connection, the syringe is altogether fixed in a ready-pack, preferably in the blister, so that no fill can emerge from the syringe.

A second object of the invention is to design a syringe that is advantageously suited for the performance of the inventive method and is easily handled during fabrication, filling, and use.

A syringe designed in accordance with these requirements is one wherein a syringe body has a cylindrical fill space, at least enclosed, open toward the rear along its entire cross-sectional area and in the front going over into a discharge cylinder, a longitudinally extended piston rod is disposed coaxial to the fill space, the rear end of said piston rod extending out of the fill space and having a handle, the front end of said piston rod having a piston which fits into the fill space so that it can be moved longitudinally, the piston has at least one piston disk, disposed frontally at the piston rod and fitting sealingly in the fill space, a closure cap is provided, which can be placed on the discharge cylinder, and which preferably can be moved along the discharge channel by a specifiable amount, and all parts consist of a material that is stable at least at 121° C., preferably a plastic. In a preferred design, behind a first piston disk, a second piston disk is present, which fits only leadingly into the fill space.

The two piston disks assure an axial guide of the piston rod both during the filling process and during use, without fabrication of the piston rod being made more difficult thereby. On the contrary, known pistons, axially extended for guidance, require more plastic material than the two piston disks provided here.

The assembled syringe is filled, in one inventive embodiment, through the open discharge cone. Dosing is here facilitated if, as is done preferably, an inner stop is provided at rear end of the inside wall which surrounds the fill space. This stop acts as a rear stop for the second piston disk when the piston is in the fill position, and it withstands the fill pressure. On the other hand, it can be overcome by the piston if greater force is exerted. When the dose intended for the fill has been reached, the fill pressure can be reduced, or it can be kept so low in advance that it does not overcome the stop. In this fashion, the dosing tolerances of the fill can be kept very tight.

The stop can be a single protrusion or also a number of protrusions disposed about the circumference, but preferably the stop is a bead concentric with the fill space.

In a preferred design of the inventive syringe, the piston rod has a circumferential seal, especially an O-ring sealing device made of rubber, which permanently assures a good seal even after autoclaving. An alternative inventive design variant is characterized in that a sealing device, which can be elastically deformed in the piston direction, and which consists especially of rubber, with at least one circumferential sealing lamella, is present frontally before the piston disk. The elastic deformability can partially intercept the pressure which builds up in the interior during the sterilization process, especially if air bubbles are present.

Advantageous modifications and developments are the subject of the other subclaims.

The features of the claims can be combined with one another in arbitrary fashion, except as they obviously exclude one another.

Further designs and advantages of the invention are elucidated by the embodiments specified below.

The invention as well as advantageous designs and developments thereof are described and elucidated in more detail below in terms of the examples shown in the drawing. The features found in the description and the drawing can be used individually or in groups in arbitrary combination.

BRIEF DESCRIPTION OF THE DRAWING

The drawing shows the following:

FIG. 1 shows a finished ready-pack in longitudinal section.

FIG. 2 shows the section 2 of FIG. 1.

FIG. 3 shows on a magnified scale the cut-out labeled FIG. 3 in FIG. 1.

WAYS TO IMPLEMENT THE INVENTION

Figure 4:
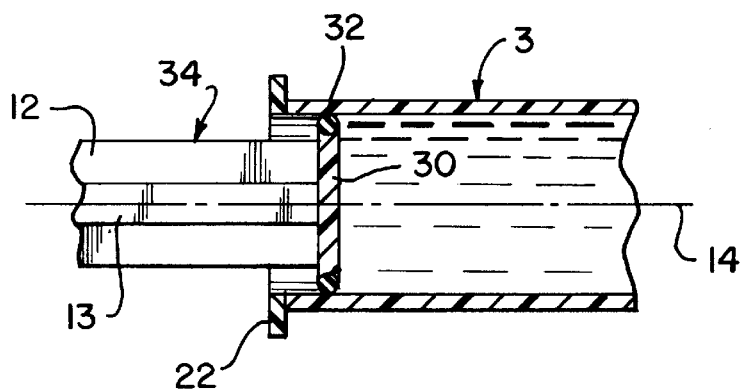
FIGS. 4, 5 schematically show a detailed section of a syringe with a piston rod and pressure means.

In the drawing, 1 generally designates the ready-pack. This consists of a syringe 3 filled with a fill 2, and a sealed, closed pack 4 for this syringe. The syringe 3 consists of the syringe body 5, the piston rod 6, and a sealing cap 7.

The syringe body 5 is cylindrical and extends longitudinally. At its rear, it has an opening 10 extending over its entire cross-sectional area. The front end of the syringe body goes over into a discharge channel body 8 with a discharge channel 9, which can be closed by the sealing cap 7, which can be attached. The syringe body encloses the fill space 11, which is filled with the flowable fill 2, preferably a liquid, gel-like, or paste-like medication, and in particular at least translucent but preferably even transparent. An oval disk 22, serving as a handle, is disposed coaxial to the syringe axis 14, at the rear end of the syringe body.

The piston rod 6 consists of two crossed, flat strips 12, 13. Its rear end extends out of the fill space 11, and there it has a pressure disk 15 as a handle, attached concentric to the syringe axis 14. Its front end has a piston 16, set into the fill space. This piston 16 consists of a first piston disk 17, disposed frontally at the piston rod, coaxial to the syringe axis 14, and of a second piston disk 18, disposed coaxial to the syringe axis 14, at some distance behind the first piston disk 17.

The first piston disk 17 fits sealingly into the fill space 11, while the second piston disk fits only guidingly into the fill space 11. The two piston disks 17 and 18 are circular in correspondence with the cross section of the fill space 11. The second piston disk 18 can have recesses along its circumference. The only important point is that it is shaped so as to provide adequate guidance. The fill 2 ends at the first piston disk 17.

The reference symbol 19 designates a bead, extending concentrically into the fill space 11, and serving as an inner stop for the second piston disk 18. This bead extends along the rear end at the inside wall of the syringe body. It forms a rear stop for the second piston disk 18, and specifically in the fill position of the piston 17. This stop withstands a fill pressure that is sufficient for filling the syringe through the discharge channel 9, but it can be overcome with a greater exertion of force by the two piston disks.

The syringe body 5 consists of plastic or of glass. The sealing cap 7 consists of rubber. The piston rod 6 consists of plastic, possibly with a stopper or an O-ring of rubber. The individual parts are all temperature-stable at 125° C., preferably at 130° C.

The pack 4—also called the blister—consists of a flat base 20 and a hood 21. The base 20 consists of stable paper, which is permeable to the diffusion of steam, but otherwise is tight. The hood 21 consists of transparent plastic. The hood and the base are stable at least up to 121° C., preferably 125° C. The pack is sufficiently stiff, so that several ready-packs can be stacked one on top of the other without the pack being pressed in. The hood 21 is tightly welded to the base 20. The hood 21 is vapor-tight.

The hood 21 is here designed such that, when the syringe is inserted, its frontal wall regions 21.1 and 21.2 lie against the front side of the pressure disk 15 and the front side of the sealing cap 7 respectively. In this way, the piston rod is prevented from escaping during the sterilization process. Heating the fill 2 and/or the air bubbles existing in the interior of the syringe body 5 causes a thermal length expansion or the build-up of an interior pressure. This could push the piston rod and the sealing cap away from the syringe body, so that the fill could exit in an undesired manner. According to the invention, this is prevented by the length expansion being at least partially prevented by the pack 1,4 itself taking up the stress due to the length expansion of the syringe 3.

Furthermore, the sealing cap 7 is disposed on the cylindrical discharge channel body 8 so as to be movable lengthwise to a predetermined extent, without the fill being able to exit from the discharge channel 9 when the sealing cap 7 moves by this predetermined path. This movability likewise counteracts a pressure which builds up in the interior of the syringe body 5.

The procedure for fabricating the ready-pack is as follows:

The syringe, fabricated under clean conditions, is held ready with the piston pushed from the front into the syringe body and with the sealing cap 7 pulled off. Liquid, gel-like, or paste-like fill material, especially a medication or a diagnostic agent, is now pressed through the discharge channel 9, and thus the piston rod 6 is pushed rearward. When the fill pressure used for this is so low that the stop formed by the bead 19 cannot be overcome, this fill pressure can be retained until the end; otherwise it is lowered shortly before reaching a complete fill to such an extent that the stop cannot be overcome. As soon as the second piston disk 18 contacts the bead 19, the fill process is completed, and the sealing cap 7 is attached.

Then the filled syringe is placed into the fabricated and prepared hood 21. Then the base 20 is attached and is welded to the hood along its entire circumference (blistering). One or more blisters are packed into folding boxes and are sterilized in an autoclave as follows.

The autoclave is first evacuated to 40 Torr. Then the autoclave chamber is heated to 125° C. by injecting steam. The pressure required for this is built up so slowly that the diffusion of steam in the intermediate space between the syringe and the pack can cause the pressure in the interior of the ready-pack to follow to such an extent that the ready-pack is not pressed in. The temperature of 125° C. is maintained until the sterilization of the fill in the container is complete. The temperature in the fill is measured and recorded by measurement sensors. In this connection at least two closed containers are always equipped with a temperature sensor in one autoclave charge. After sterilization, the sterilized material in the chamber is cooled indirectly. To remove impermissible residual moisture, the autoclave chamber is evacuated once or several times during and after the cooling process. It is then cooled to the outside temperature, is vented, and is opened. The cooling process takes place slowly, while a support pressure generated by air is introduced simultaneously, and in such a way that the pressure can equalize in the interior of the ready-pack, without the hood being pressed in thereby.

Figure 5:
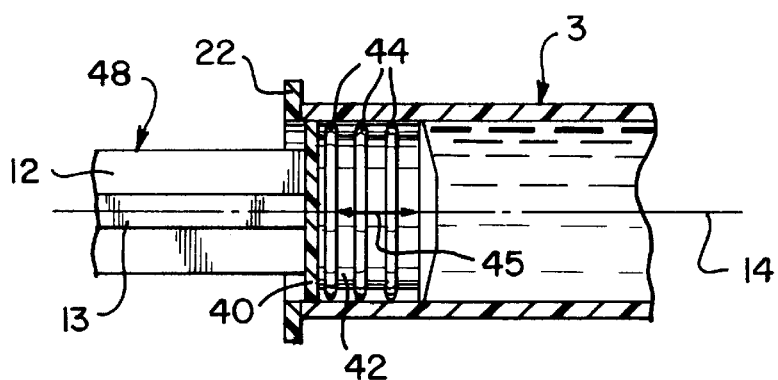

In the regional longitudinal section shown in FIGS. 4 and 5, what is involved is the seal of the piston rod 6 inside the syringe 3. The same components bear the same reference symbols and will not be explained again.

The piston rod 34, shown in FIG. 4, has a piston disk 30, which has a groove along its circumference, in which is mounted an O-sealing ring 32 made of rubber. The O-ring 32 assures adequate tightness even after autoclaving despite shrinkage of the piston rod itself, which can happen occasionally.

The piston rod 48, shown by way of a cut-out in FIG. 5, has a circular disk 40, at whose front side a rubber stopper 42 is disposed as a sealing device. This rubber stopper has three elastic sealing lamellas 44 extending lengthwise. The rubber stopper can be elastically deformed in the longitudinal direction (arrow 45), so that this property can at least partly counteract a pressure which builds up in the interior of the syringe 3 during the sterilization process.

Figure 6:
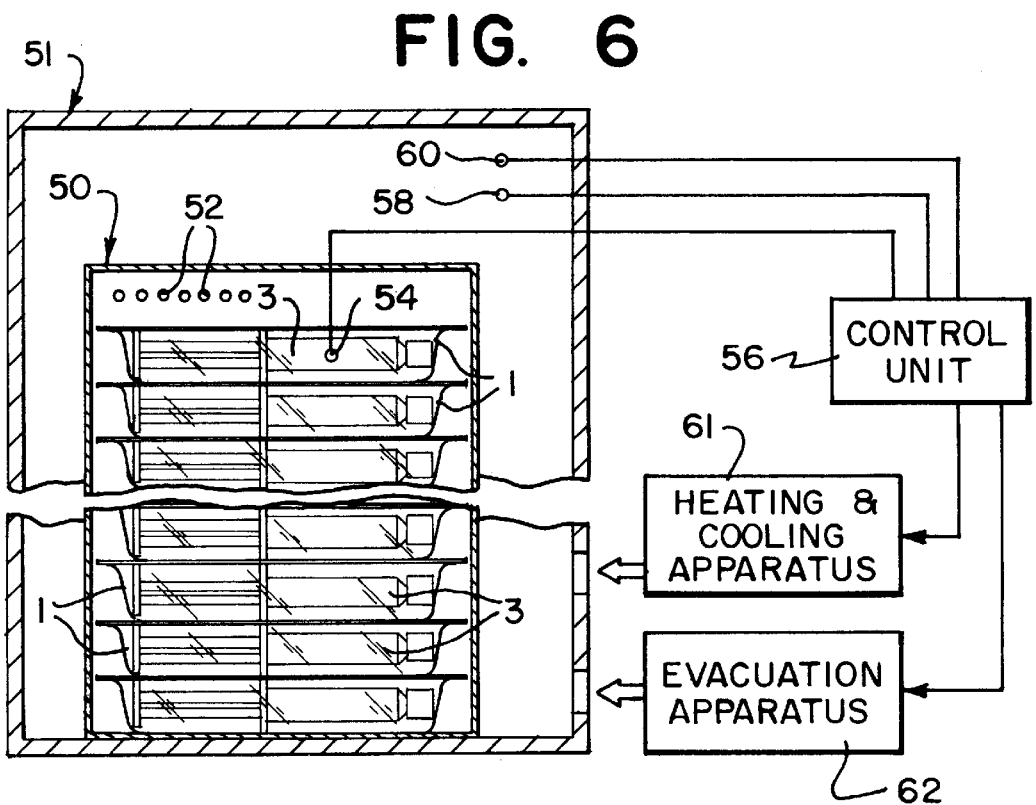
FIG. 6 schematically shows a section through an autoclave with a packing unit containing several ready-packs, with temperature-, pressure-, and moisture-measurement during autoclaving.

FIG. 6 schematically shows an autoclave 51, into which a packing unit 50 has been placed for autoclaving. This packing unit 50 contains several ready-packs 1 which are equipped with a filled syringe. The packing ring 50 consists of at least one folding box, which in some areas has a perforation 52, as shown schematically in FIG. 6. In at least two ready-packs 1.1 in each autoclave charge, a temperature sensor 54 is present in the interior of the syringe 3, to measure the temperature of the medication filled into the syringe body, during the autoclaving process. This temperature sensor 54 delivers a signal to a control unit 56, which acts on a heating apparatus and a cooling apparatus 64 and, as necessary, causes increased heating if the temperature is too low and causes the controlled cooling of the autoclave charge after sterilization.

In a special embodiment, a plurality (e.g. 1,000) folding boxes 50, each charge with ten blisters 1, are steam-sterilized in an autoclave 51. The temperature is here sensed and controlled (regulated) by means of a measurement sensor 54 in two syringes 3, distributed over the sterilization material (e.g. on the top and in the middle). Furthermore, a pressure sensor 58 and a moisture sensor 60 are present in the autoclave 51. These likewise deliver their signals to the control device 56. The control device 56 acts, as necessary, on an evacuation apparatus 62 in dependence on the signals from the pressure sensor 58 and the moisture sensor 60. The evacuation apparatus 62 makes it possible to reduce the pressure at a specified rate. The moisture content is compared with an empirically determined value, said value being determined such that as little condensate as possible is produced, and such that so much moisture is present in the steam-air mixture that good heat transfer takes place to the fill in the container so as to provide fast and perfect sterilization, and, on the other hand, as little condensate as possible is formed, so that no visual impairments (water spots) appear at the blister and at the folding box and so that no residual moisture remains in the pack.

With this packing unit 50, the ready-pack, the outside of the syringe, and the fill in the syringe are sterilized in one step. An expensive, aseptic fill process is thus obviated. Furthermore, the inventive method makes it possible that the preservatives, frequently used to preserve the fill, are not needed, since the sterilization process can assure a sufficiently long storage time, without deterioration of the effectiveness of the fill. Allergic reactions which could occur from the preservatives thus can be avoided.

The inventive method thus can also be used preferably for filled glass syringes or for other medical utility articles, for which sterility is required not only for the fill, i.e. the medication itself, but also an external sterility, namely preferably in areas of a clinic, in which such ready-packs are needed or used intra-operatively, i.e. in operating rooms for operations on the open body.

I claim:

1. A method for preparing a sterile ready-pack unit including at least one sterilized ready-pack containing a syringe closed off at one end and made from thermally stable material withstanding up to 130° C., for single use application, said method comprising the step of:

filling a water-containing pharmaceutical substance through an open end into the syringe by utilizing pressure;

closing the open end of the syringe off with a thermally stable cap withstanding up to 130° C.;

inserting the filled syringe into said ready-pack, having a steam-permeable base;

placing the ready-pack into an autoclave;

controllably heating the ready-pack unit in an autoclave by circulating steam-air mixture at a temperature of at least about 120° C. to 130° C. for at least about 15 minutes, so as to simultaneously sterilize the at least one ready-pack, the container and the substance within the container.

2. The method according to claim 1, wherein the duration of time is at least 20 minutes.

3. The method of claim 1, wherein the at least one non-sterilized ready-pack is a plurality of ready-packs.

4. The method of claim 1, further comprising the steps of controlling the autoclave pressure and the moisture of the steam-air mixture during the sterilizing step.

5. The method of claim 1, wherein the ready-pack unit is a folding box and the base is perforated cardboard.

6. The method of claim 1, wherein the base is paper.

7. A method for sterilizing a ready-pack unit, including at least one sealed blister pack containing a syringe with a discharge piston, the syringe containing a water-containing pharmaceutical substance and being made from thermally stable material withstanding up to 130° C., the blister pack having a steam-permeable base, comprising the steps of:

heating the sealed blister-pack with steam to a temperature of about 121° C. for at least about 20 minutes in an autoclave environment, under vacuum conditions, increasing the pressure in the autoclave to atmospheric while cooling down the ready-pack unit, and drying the ready-pack unit by evacuating the autoclave.

8. A method for sterilizing a ready-pack unit having semi-permeable base, and, sealed within, a syringe cylinder including an injection needle and a discharge piston, and made from thermally stable material withstanding up to 130° C., said cylinder being filled with an injectable water-containing pharmaceutical substance, comprising the steps of:

sterilizing the ready-pack in an autoclave, under vacuum, at a temperature of about 121° C. for at least about 20 minutes; and increasing the pressure in the autoclave to atmospheric while cooling down the ready-pack unit.

* * * * *